United States Patent [19]

Waldstreicher

[11] Patent Number: 5,730,964

[45] Date of Patent: *Mar. 24, 1998

[54] METHOD OF TREATING SWEAT-RELATED CONDITIONS

[75] Inventor: Joanne Waldstreicher, Scotch Plains, N.J.

[73] Assignee: Merck & Co., Inc., Rahway, N.J.

[*] Notice: The term of this patent shall not extend beyond the expiration date of Pat. No. 5,512,555.

[21] Appl. No.: 750,464

[22] PCT Filed: Jun. 2, 1995

[86] PCT No.: PCT/US95/06679

§ 371 Date: Dec. 9, 1996

§ 102(e) Date: Dec. 9, 1996

[87] PCT Pub. No.: WO96/03129

PCT Pub. Date: Feb. 8, 1996

[51] Int. Cl.$^6$ .............. A61K 7/32; A61K 7/38; A61K 31/58; A61K 31/44

[52] U.S. Cl. .............. 424/65; 424/68; 514/176; 514/284; 514/570

[58] Field of Search .............. 424/65, 68; 514/176, 514/284, 570

[56] References Cited

U.S. PATENT DOCUMENTS

| | | | |
|---|---|---|---|
| 4,760,071 | 7/1988 | Rasmusson et al. | 514/284 |
| 5,512,555 | 4/1996 | Waldstreicher | 514/168 |

FOREIGN PATENT DOCUMENTS

WO93/23419  11/1993  WIPO.

OTHER PUBLICATIONS

Takayasu et al., "Activity of testosterone 5alpha-reductase in various tissues of human skin", J. Invest. Dermatol., vol. 74, pp. 187–191 (1980).

Mortimer et al., "A double-blind controlled cross-over trial of cypoterone acetate in females with hidradenitis suppurativa", British J. Dermatol., vol. 115, pp. 263–268 (1986).

Sawers et al., "Control of hiradenitis suppurativa in women using combined antiandrogen (cyproterone acetate) and oestrogen therapy", British J. Dermatol., vol. 115, pp. 269–274 (1986).

Harris et al., "Identification and selective inhibition of an isozyme of steroid 5-alpha reductase in human scalp", Proc. Natl. Acad. Sci., vol. 89, pp. 10787–10792 (1992).

Primary Examiner—Kimberly Jordan
Attorney, Agent, or Firm—Catherine D. Fitch; Melvin Winokur

[57] ABSTRACT

The instant invention involves methods of treating sweat related conditions with compounds that are 5α-reductase inhibitors. The 5α-reductase inhibitors may be administered alone or in combination with other active agents to treat conditions such as apocrine gland sweating, hyperhidrosis, and hydradenitis suppurativa.

16 Claims, No Drawings

METHOD OF TREATING SWEAT-RELATED CONDITIONS

This application is a 371 of PCT/US 95/06679, filed Jun. 2, 1995.

The present invention is concerned with the treatment of sweat-related conditions with compounds that are 5α-reductase inhibitors.

BACKGROUND OF THE INVENTION

Apocrine sweat glands, comprised of ducts that open directly into the hair follicle, are largely confined to regions of the axilla and perineum (genital-anal area) and become functional just before puberty. Although this suggests that gonadal steroids (i.e. androgens and estrogens) play a role in their development, the exact hormones have not been identified.

In man, the role of the apocrine gland is unclear, since the eccrine sweat glands (which open directly onto the surface of the skin and which are distributed over nearly the entire body surface) perform the thermoregulatory function. The odor, which results from bacterial action on aprocrine sweat, may have had a role in man in the past, but is now clearly vestigial. Sweat collected from the surface of the skin is contaminated by sebum (since there is a common opening to the surface of the skin), secretions from eccrine sweat glands, as well as bacteria. Based on animal data, it is thought that aprocrine sweat contains protein, nitrogen, potassium, sodium, calcium, magnesium, chloride, bicarbonate and lactate. Sweat is secreted in a pulsatile manner, presumably due to synchronous contraction of myoepithelial cells across the body.

Unlike eccrine glands which are under cholinergic control, apocrine gland secretion is largely under adrenergic control. Both local and circulating epinephrine and norepinephrine can stimulate secretion. Emotional stimuli, after puberty, are strong inducers of secretion. Drugs that affect the adrenergic system (such as reserpine) affect apocrine gland secretion. 5α-Reductase levels are very high in apocrine glands. Therefore, activity of this enzyme is believed to play a role in controlling secretion. However, a 5α-reductase inhibitor has not been previously studied as an inhibitor of apocrine secretion.

Hyperhidrosis is defined as an increase above normal in sweat production. This is diagnosed when sweating occurs under conditions where it would not normally be expected or is excessive in response to emotional or thermal stimuli.

Localized hyperhidrosis of the axilla is most likely due to a combination of increased eccrine and apocrine sweat production. This disorder is usually most problematic when there is both an increased ambient temperature and emotional stimulation. Axillary sweating, unlike eccrine sweating, is largely resistant to most common antiperspirant regimens. Aluminum salts or anticholinergic agents produce only a 50% decrease in armpit sweating, but nearly a 100% decrease in eccrine sweating elsewhere. However, Shelley described a regimen of aluminum chloride in absolute ethanol or isopropyl alcohol under occlusive plastic wrap at bedtime which more effectively inhibits axillary sweat. Other reported treatments are sympathectomy of the fifth thoracic ganglion, local excision of affected axillary skin, cryosurgery, tranquilizers and anticholinergic agents.

Hydradenitis suppurativa (HS) is a chronic inflammatory disorder of apocrine sweat glands in which abscesses and drainage sinuses develop in the axilla and/or perineal area. The pathogenesis of HS is felt to be similar to acne: poral occlusion, bacterial colonization, androgenic stimulation and intimation all seem to be important. Although its etiology is multifactorial, it is likely that a change in any one of the four etiologic factors will have a significant impact on the course of the disease. Antibiotics (affecting bacterial colonization) and isotretinoin (ACCUTANE®) (affecting the keratinous plugging of the sweat duct) are used to treat this disorder. Antiandrogens such as cyproterone (not available in the U.S.) and estrogen have also been used to control HS.

The enzyme 5α-reductase converts testosterone ("T") to dihydrotestosterone in certain target organs as well as in the circulating blood serum. It is known that inhibitors of 5α-reductase will serve to prevent or lessen symptoms of hyperandrogenic stimulation such as acne vulgaris, seborrhea, female hirsutism, androgenic alopecia, and benign prostatic hyperplasia. See especially U.S. Pat. Nos. 4,377,584 and 4,760,071, both assigned to Merck & Co., Inc. It is also now known that two isozymes of 5α-reductase exist: isozyme type 2 which principally interacts within prostatic tissues, and isozyme type 1, discovered more recently, which principally interacts within skin tissues. See, e.g., G. Harris, et al., Proc. Natl. Acad. Sci. USA, vol. 89, pp. 10787–10791 (November 1992).

Since androgens are felt to play a role in the pubertal onset of aprocrine gland function and the pathogenesis of HS and there is a large amount of 5α-reductase activity in apocrine sweat glands, apocrine sweat gland production should be decreased by 5α-reductase inhibitors, such as finasteride (marketed in the U.S. under the tradename PROSCAR® for the treatment of benign prostatic hyperplasia) and 4,7β-dimethyl-4-aza-5α-cholestan-3-one (also known as MK-386). A decrease in sweat production, should be observed with either oral administration or topical application of 5α-reductase inhibitors to the axillae or perineum. Therefore, these agents will be useful as antiperspirants and for the treatment of other androgenmediated conditions related to sweat glands, such as local hyperhidrosis and HS.

SUMMARY OF THE INVENTION

The instant invention involves a novel method of treating sweat-related conditions, such as apocrine gland sweating, also known as perspiration, hyperhidrosis and HS comprising the administration of a therapeutically effective amount of a 5α-reductase inhibitor. Also provided are pharmaceutical compositions comprising a pharmaceutically acceptable carrier, a 5α-reductase inhibitor and additional active agents such as aluminum hydroxide, anticholinergic agents, antibiotics, and isotretinoin which are useful for the treatment of sweat-related conditions.

DETAILED DESCRIPTION OF THE INVENTION

The present invention has the objective of providing methods of treating sweat-related conditions including aprocrine gland sweating, hyperhidrosis and hydradenitis suppurativa (HS) by oral, systemic, parenteral or topical administration of a 5α-reductase inhibitor or a combination of 5α-reductase inhibitors, either alone or in combination with other active agents such as aluminum hydroxide, anticholinergic agents, antibiotics and isotretinoin.

The term "5α-reductase inhibitor" as used herein is intended to include compounds which are active as inhibitors of either or both of the isozymes of 5α-reductase, such as, e.g., inhibitors of 5α-reductase type 1, such as e.g., 4,7β-dimethyl-4-aza-5α-cholestan-3-one (also known as MK-386; as disclosed in WO 93/23420 to Merck & Co. Inc.), 3-oxo-4-aza-4,7β-dimethyl-16β-(phenoxy)-5α-androstane, and 3-oxo-4-aza-4,7β-dimethyl-16β-(4-chlorophenoxy)-5α-androstane (both disclosed in PCT application Serial No. US 94/12071), inhibitors of 5α-reductase type 2, such as e.g., finasteride, epristeride (also known as SKF-105657, SmithKline Beecham), ONO-3805 (Ono Pharmaceutical Co., Ltd.), FK-143 (Fujisawa), and TZP-4238 (Teikokuzoki), and those which are active as dual inhibitors of both isozymes type 1 and 2, such as e.g., those disclosed in WO 94/00121 and WO94/00125 to Smith-Kline Beecham. Also encompassed by the instant method invention is the use of a combination of an inhibitor of 5α-reductase type 1 with an inhibitor of 5α-reductase type 2, such as e.g., the use of a combination of finasteride with MK-386. Many compounds which are 5α-reductase inhibitors have been described in the art; compounds which are 5αreductase inhibitors can also be determined by the 5α-reductase assay further described below.

Examples of compounds specifically and generically which are 5α-reductase inhibitors and the use of which are encompassed within the present invention, include, but are not limited to, those described in the following patents and publications: U.S. Pat. No's: 4,377,584; 4,760,071; 4,845,104; 4,859,681; 5,049,562; 5,120,742; 5,138,063; and 5,151,429; and WO 93/23038, WO 93/23039, WO 93/23040, WO 93/2304 1, WO 93/23048, WO 93/23050, WO 93/23051, WO 93/23419, WO 93/23420, WO 93/16996, WO 93/23042, WO 94/00121, WO 94/00125, WO 94/03474, WO 94/03475, WO 94/03476, WO 94/07909, WO 93/13124, U.S. Pat. No. 5,302,528, EP 532,190, EP 291,245, and PCT application U.S. Ser. No. 94/12071. The above list is not intended to be exhaustive, and there are many other publications which describe inhibitors of 5α-reductase.

The term "therapeutically effective amount" means that amount of a drug or pharmaceutical agent that will elicit the biological or medical response of a tissue, system, animal or human that is being sought by a researcher, veterinarian, medical doctor or their clinician. The novel methods of treatment of this invention are for conditions known to those skilled in the art. In fact, apocrine gland sweating, or perspiration, is a condition commonly known and understood by average consumers who lack any specialized medical skills.

In particular, with regard to treating the disorders of hyperhidrosis and hydradenitis suppurativa, the term "therapeutically effective amount" is intended to mean that amount of a 5α-reductase inhibitor or combination of inhibitors that will prevent or alleviate the symptoms of the disorder. With regard to treating the condition of aprocrine gland sweating, i.e., for use of a 5α-reductase inhibitor or combination of inhibitors as an anti-perspirant, the term "therapeutically effective amount" is intended to mean that amount of inhibitor that will prevent or reduce the amount of apocrine gland secretions.

The present invention also has the objective of providing suitable topical, oral, systemic and parenteral pharmaceutical formulations for use in the novel methods of treatment of the present invention. The compositions containing 5α-reductase inhibitor compounds as the active ingredient for use in the treatment of the above-noted conditions can be administered in a wide variety of therapeutic dosage forms in conventional vehicles for systemic administration. For example, the compounds can be administered in such oral dosage forms as tablets, capsules (each including timed release and sustained release formulations), pills, powders, granules, elixirs, tinctures, solutions, suspensions, syrups and emulsions, or by injection. Likewise, they may also be administered in intravenous (both bolus and infusion), intraperitoneal, subcutaneous, topical with or without occlusion, or intramuscular form, all using forms well known to those of ordinary skill in the pharmaceutical arts.

The daily dosage of the compounds may be varied over a range from 0.01 to 1,000 mg per adult human/per day. For oral administration, the compositions are preferably provided in the form of tablets containing 0.01, 0.05, 0.1, 0.5, 1.0, 2.5, 5.0, 10.0, 15.0, 25.0, and 50.0 milligrams of the active ingredient for the symptomatic adjustment of the dosage to the patient to be treated. An effective amount of the drug is ordinarily supplied at a dosage level of from about 0.0002 mg./kg. to about 50 mg./kg. of body weight per day. The range is more particularly from about 0.001 mg./kg. to 7 mg./kg. of body weight per day.

Advantageously, compounds of the present invention may be administered in a single daily dose, or the total daily dosage may be administered in divided doses of two, three or four times daily. Furthermore, compounds for the present invention can be administered in intranasal form via use of suitable intranasal vehicles, or via transdermal routes, using those forms of transdermal skin patches well known to those of ordinary skill in that art. To be administered in the form of a transdermal delivery system, the dosage administration will, of course, be continuous rather than intermittent throughout the dosage regimen.

For the treatment of sweat-related conditions, the compounds of the present invention may be administered in a pharmaceutical composition comprising the active compound in combination with a pharmaceutically acceptable carrier adapted for topical administration. Topical pharmaceutical compositions may be, e.g., in the form of a solution, cream, ointment, gel, lotion, or aerosol formulation adapted for application to the skin. These topical pharmaceutical compositions containing the compounds of the present invention ordinarily include about 0.005% to 5% by weight of the active compound in admixture with a pharmaceutically acceptable vehicle.

For the treatment of apocrine gland sweating and hyperhidrosis, the 5α-reductase inhibitor compounds can be used in combination with a therapeutically effective amount of a topical antiperspirant such as an aluminum salt, e.g. aluminum hydroxide and/or a topical or oral anti-cholinergic agent and optionally including a deodorant. For the treatment of HS, the 5α-reductase inhibitor compounds can be used in combination with an anticholinergic agent, antibiotics and/or isotretinoin each of which can be administered topically or orally. Where combination treatment is employed, the active agents may be administered in a single pharmaceutical dosage formulation. Alternatively, a combined therapy can be employed wherein the active agents are administered in separate dosage formulations. For example, a 5α-reductase inhibitor and aluminum hydroxide can be administered in a single topical dosage formulation, or each active agent can be administered in a separate dosage formulation, e.g., an oral dosage formulation of the 5α-reductase inhibitor in combination with a topical dosage formulation of aluminum hydroxide. See, e.g., U.S. Pat. Nos. 4,377,584 and 4,760,071 which describe dosages and formulations for 5α-reductase inhibitors.

For combination treatment with more than one active agent, where the active agents are in separate dosage formulations, the active agents can be administered concurrently, or they each can be administered at separately staggered times.

The dosage regimen utilizing the compounds of the present invention is selected in accordance with a variety of factors including type, species, age, weight, sex and medical condition of the patient; the severity of the condition to be treated; the route of administration; the renal and hepatic function of the patient; and the particular compound thereof employed. A physician or veterinarian of ordinary skill can readily determine and prescribe the effective amount of the drug required to prevent, counter or arrest the progress of the condition. Optimal precision in achieving concentration of drug within the range that yields efficacy without toxicity requires a regimen based on the kinetics of the drug's availability to target sites. This involves a consideration of the distribution, equilibrium, and elimination of a drug.

In the methods of the present invention, the compounds herein described in detail can form the active ingredient, and are typically administered in admixture with suitable pharmaceutical diluents, excipients or carriers (collectively referred to herein as "carrier" materials) suitably selected with respect to the intended form of administration, that is, oral tablets, capsules, elixirs, syrups and the like, and consistent with conventional pharmaceutical practices.

For instance, for oral administration in the form of a tablet or capsule, the active drug component can be combined with an oral, non-toxic pharmaceutically acceptable inert carrier such as ethanol, glycerol, water and the like. Moreover, when desired or necessary, suitable binders, lubricants, disintegrating agents and coloring agents can also be incorporated into the mixture. Suitable binders include, without limitation, starch, gelatin, natural sugars such as glucose or beta-lactose, corn sweeteners, natural and synthetic gums such as acacia, tragacanth or sodium alginate, carboxymethylcellulose, polyethylene glycol, waxes and the like. Lubricants used in these dosage forms include, without limitation, sodium oleate, sodium stearate, magnesium stearate, sodium benzoate, sodium acetate, sodium chloride and the like. Disintegrators include, without limitation, starch, methyl cellulose, agar, bentonite, xanthan gum and the like.

The liquid forms in suitably flavored suspending or dispersing agents such as the synthetic and natural gums, for example, tragacanth, acacia, methyl-cellulose and the like. Other dispersing agents which may be employed include glycerin and the like. For parenteral administration, sterile suspensions and solutions are desired. Isotonic preparations which generally contain suitable preservatives are employed when intravenous administration is desired.

Topical preparations containing the active drug component can be admixed with a variety of carrier materials well known in the art, such as, e.g., alcohols, aloe vera gel, allantoin, glycerine, vitamin A and E oils, mineral oil, PPG2 myristyl propionate, and the like, to form, e.g., alcoholic solutions, topical cleansers, cleansing creams, skin gels, skin lotions, aerosol or non-aerosal sprays, and shampoos in cream or gel formulations. See, e.g., EP 0 285 382.

The compounds of the present invention can also be administered in the form of liposome delivery systems, such as small unilamellar vesicles, large unilamellar vesicles and multilamellar vesicles. Liposomes can be formed from a variety of phospholipids, such as cholesterol, stearylamine or phosphatidylcholines.

The compounds of the present invention may be coupled to a class of biodegradable polymers useful in achieving controlled release of a drug, for example, polylactic acid, polyepsilon caprolactone, polyhydroxy butyric acid, polyorthoesters, polyacetals, polydihydro-pyrans, polycyanoacrylates and cross-linked or amphipathic block copolymers of hydrogels.

EXAMPLE 1

BIOLOGICAL ASSAYS

Preparation of Human Prostatic and Scalp 5α-reductases

Samples of human tissue were pulverized using a freezer mill and homogenized in 40 mM potassium phosphate, pH 6.5, 5 mM magnesium sulfate, 25 mM potassium chloride, 1 mM phenylmethylsulfonyl fluoride, 1 mM dithiothreitol (DTT) containing 0.25M sucrose using a Potter-Elvehjem homogenizer. A crude nuclear pellet was prepared by centrifugation of the homogenate at 1,500×g for 15 min. The crude nuclear pellet was washed two times and resuspended in two volumes of buffer. Glycerol was added to the resuspended pellet to a final concentration of 20%. The enzyme suspension was frozen in aliquots at −80° C. The prostatic and scalp reductases were stable for at least 4 months when stored under these conditions.

5α-reductase assay

The reaction mixture for the type 1 5α-reductase contained 40 mM potassium phosphate, pH 6.5, 5 mM [7-$^3$H]-testosterone, 1 mM dithiothreitol and 500 μM NADPH in a final volume of 100 μl. The reaction mixture for the type 2 5α-reductase contained 40 mM sodium citrate, pH 5.5, 0.3 mM [7-$^3$H]-testosterone, 1 mM dithiothreitol and 500 μM NADPH in a final volume of 100 μl. Typically, the assay was initiated by the addition of 50–100 μg prostatic homogenate or 75–200 μg scalp homogenate and incubated at 37° C. After 10–50 min. the reaction was quenched by extraction with 250 μl of a mixture of 70% cyclohexane: 30% ethyl acetate containing 10 μg each DHT and T. The aqueous and organic layers were separated by centrifugation at 14,000 rpm in an Eppendoff microfuge. The organic layer was subjected to normal phase HPLC (high pressure liquid chromatography) (10 cm WHATMAN PARTISIL 5 silica column equilibrated in 1 ml/min 70% cyclohexane: 30% ethyl acetate; retention times: DHT, 6.8–7.2 min.; androstanediol, 7.6–8.0 min.; T, 9.1–9.7 min.). The HPLC system consisted of a WATERS Model 680 Gradient System equipped with a HITACHI Model 655α autosampler, APPLIED BIOSYSTEMS Model 757 variable UV detector, and a RADIOMATIC Model A120 radioactivity analyzer. The conversion of T to DHT was monitored using the radioactivity flow detector by mixing the HPLC effluent with one volume of FLO SCINT 1 (RADIOMATIC). Under the conditions described, the production of DHT was linear for at least 25 min. The only steroids observed with the human prostate and scalp preparations were T, DHT and androstanediol.

Inhibition Studies

Compounds were dissolved in 100% ethanol. The compound to be tested was pre-incubated with the enzyme (either 5α-reductase type 1 or 2) prior to initiation by addition of substrate testosterone. $IC_{50}$ values represent the concentration of inhibitor required to decrease enzyme conversion of testosterone to dihydrotestosterone by 50% of the control. $IC_{50}$ values were determined using a 6 point titration where the concentration of the inhibitor was varied from 0.1 to 1000 nM.

A compound referred to herein as a 5α-reductase 2 inhibitor is a compound that shows inhibition of the 5α-reductase 2 isozyme in the above-described assay, having an $IC_{50}$ value of about or under 100 nM.

A compound referred to herein as a 5α-reductase type 1 inhibitor is a compound that shows inhibition of the 5α-reductase type 1 isozyme in the above-described assay, having an $IC_{50}$ value of about or under 100 nM.

A compound referred to herein as a dual 5α-reductase type 1 and 2 inhibitor is a compound that shows inhibition of both the type 1 and type 2 isozymes, having an $IC_{50}$ value of about or under 100 nM for each isozyme.

EXAMPLE 2

3-Oxo 4-aza-4,7β-dimethyl-16β-(4-chlorophenoxy)-5α-androstane

The starting material 4-aza-4,7β-dimethyl-5α-androstan-3,17-dione may be synthesized according to the procedure described in Example 3, below Step 1: 4-aza-4,7β-dimethyl-5α-androstan-3,17-dione-16-oxime To 2-methyl-2-propanol (28 mL) in a round-bottom flask under a stream of nitrogen gas was added potassium tert-butoxide (1.35 g, 12.1 mmol). After complete solution was achieved, 4-aza-4,7β-dimethyl-5α-androstan-3,17-dione (1.92 g, 6.0 mmol) was added and stirring was continued for 1 hour affording a gold-colored solution. To the reaction mixture was added dropwise with stirring isoamyl nitrite (1.63 mL, 12.1 mmol), and stirring was continued overnight at room temperature affording a deep-orange solution. The mixture was then diluted with an equal volume of water, acidified to pH ~2 with 2 N hydrochloric acid, and extracted with diethyl ether (3×50 mL). The combined ether extracts were washed with saturated brine solution, dried (sodium sulfate), and evaporated. The crude product was subjected to flash silica gel chromatography using 5% methanol/methylene chloride as eluant to yield the title compound.

Step 2: 4-aza-4,7β-dimethyl-5α-androstan-3-one-16-oxime

To a mixture of 4-aza-4,7β-dimethyl-5α-androstan-3,17-dione-16-oxime (2.7 g, 7.79 mnol) in ethylene glycol (30 mL) were added 98% hydrazine (0.27 mL, 8.57 mmol) and powdered potassium hydroxide (2.62 g, 46.8 mmol). The mixture was heated for 3 h at 140°, cooled, diluted with water (100 mL), neutralized with concentrated hydrochloric acid to give a tan precipitate that was filtered and dried (1.7 g). Flash silica gel chromatography of this material using initially 2% methanol/methylene chloride and subsequently 5% methanol/methylene chloride as eluant gave pure product.

Step 3: 4-aza-4,7β-dimethyl-5α-androstan-3,16-dione

A mixture of 4-aza-4,7β-dimethyl-5α-androstan-3-one-16-oxime (0.55 g, 1.65 mmol) in 60% acetic acid (20 mL) was heated at reflux temperature for 48 hours. The cooled mixture was diluted with water (25 mL) and extracted with methylene chloride (3×50 mL). The combined extracts were washed with saturated sodium hydrogen-carbonate solution, dried (sodium sulfate), and evaporated. Flash silica gel chromatography using 2% methanol/methylene chloride afforded pure product; mass spectrum: m/z 317 (M). 400 MHz $^1$H NMR (CDCl$_3$): δ 0.88 (s, 3H); 0.89 (s, 3H); 1.00 (d, 3H); 2.90 (s, 3H); and 3.07 (dd, 1H).

Step 4: 3-Oxo-4-aza-4,7β-dimethyl-16β-hydroxy-5α-androstane

A solution of 4-aza-4,7β-dimethyl-5α-androstan-3,16-dione (390 mg, 1.23 mmol) in methanol (8 mL) was cooled in an ice bath and treated with sodium borohydride (140 mg, 3.68 mmol) for 30 min. The reaction mixture was diluted with water and extracted with methylene chloride (3×50 mL). The combined organic extracts were washed with saturated brine solution, dried (Na$_2$SO$_4$), and evaporated. The desired product was purified by flash silica gel chromatography using initially 10% acetone/methylene chloride and subsequently 20% acetone/methylene chloride as eluant to yield the title compound; mass spectrum: m/z 391(M). 400 MHz $^1$H NMR (CDCl$_3$): δ 0.83 (s, 3H); 0.96 (s, 3H); 1.03 (d, 3H); 2.90 (s, 3H); 3.00 (dd, 1H); and 4.36 (m, 1H).

Step 5: 3-Oxo-4-aza-4,7β-dimethyl-16β-(4-chlorophenoxy)-5α-androstane

To a solution of 3-oxo-4-aza-4,7β-dimethyl-16β-hydroxy-5α-androstane (20 mg,0.063 mmol) in N,N-dimethylformamide (0.5 mL) is added powdered potassium hydride (35 weight %) (15 mg, 0.126 mmol). After stirring for 15 min at room temperature under an nitrogen atmosphere, 1-chloro-4-fluorobenzene (0.315 mmol) is added and stirring is continued for 2 hours at room temperature. The mixture is diluted with methylene chloride (25 mL) and quenched in ice-water. The aqueous layer is extracted with methylene chloride (3×25 mL) and the combined organic layers are washed with saturated brine solution, dried (sodium sulfate) and evaporated. The desired product is purified by flash silica gel chromatography to yield the title compound; mass spectrum: m/z 430 (M+1). 400 MHz $^1$H NMR (CDCl$_3$): δ 0.85 (s, 3H); 0.93 (s, 3H); 1.03 (d, 3H); 2.90 (s, 3H); 3.02 (dd, 1H); 5.28 (m, 1H); 6.74 (d, 2H); and 7.19 (d, 2H).

EXAMPLE 3

3-Oxo-4-aza-4,7β-dimethyl-16β-(phenoxy)-5α-androstane

Starting with the product of Example 2, Step 4, and essentially following the procedures of Example 2, Step 5, substituting fluorobenzene for 1-chloro-4-fluorobenzene, the title compound is prepared.

EXAMPLE 4

Preparation of Starting material 4-aza-4,7β-dimethyl-5α-androstan-3, 17-dione

Step 1: Synthesis of 3-Acetoxy-Androst-5-en-17-ol.

To a solution of 100 mg. (0.303 mmol) of 3-acetoxy-androst-5-en-17-one in 3 ml EtOH at −10° C., was added 22.9 mg (0.606 mmol) of sodium borohydride with stirring. After the reaction mixture was stirred for one and ½ hours, the mixture was diluted with 10 ml water, the ethanol solvent removed under vacuum, and the residue extracted with ethyl acetate. The organic layer was washed with aqueous Na$_2$CO$_3$, brine, dried over sodium sulfate and concentrated to leave a residue of crude title compound. Proton NMR confirmed the assigned structure.

Step 2: Synthesis of 3-Acetoxy-Androst-5-en-17-ol, 17-t-butyl-dimethyl-silyl ether To a solution of the androstan-17-ol, from the previous synthesis, being 4.5 g (13.55 mmol) in 50 ml. dimethylformamide at 23° C. was added 2.76 g (40–65 mmol) imidazole followed by 3.063 g (20.32 mmol) of t-butyldimethylsilyl chloride. The reaction mixture was stirred and a solid began to precipitate. Twenty additional ml of DMF were added and the mixture further stirred overnight. The mixture was poured into 1 liter water, the solid filtered and washed with water. The solid was dissolved in ethylacetate, the organic layer washed with brine and dried over sodium sulfate, concentrated to yield the silyl protected 17-ol title compound. The proton NMR confirmed the assigned structure.

Step 3: 7-one-17β-ol, 17-t-butyldimethylsilyl ether

To a solution of the TBMS protected 17-ol from the previous synthesis, being 5.6 g (12.55 mmol) in 100 ml acetonitrile at 23° C. was added 90% t-butyl hydrogen peroxide, 3.958 g (43.92 mol), and 138 mg chromium hexacarbonyl. After refluxing the mixture under nitrogen for 24 hours, the reaction mixture was poured into one liter water, solid was filtered, the residue washed with 500 ml water and the residue dissolved in 350 ml methylene chloride. The organic layer was washed with brine, dried over sodium sulfate and concentrated to yield crude material. Thin layer chromatography (3:1 hexane/ethyl acetate on silica gel) showed the presence of starting material. The solid was purified by column chromatography over silica gel by elution with 7% ethyl acetate/hexane to yield the title compound. Proton NMR confirmed the assigned structure.

Step 4: Synthesis of 3,7-dihydroxy-7-methyl-androst-5-en-17β-ol, 17-t-butyldimethylsilyl ether To a solution of the product from the previous synthesis, being 440 mg. (0.956 mmol) in dry tetrahydrofuran at 0° C. was added dropwise methyl magnesium chloride over 5–10 minutes. The reaction mixture was then allowed to stir at room temperature for 24 hours, then poured into saturated aqueous ammonium chloride. The THF solvent was removed under vacuum and the aqueous phase extracted with ethyl acetate. The organic layer was washed with brine, dried, concentrated to yield crude product. Proton NMR confkrmed the assigned structure of the title compound which was used in the next step without further purification.

Step 5: Synthesis of 7-methyl-androst-4,6-dien-3-one-17β-ol, 17-t-butyldimethylsilyl ether The above Grignard product, 3.5 g. (7.142 mmol) was dissolved in 50 ml toluene/50 ml. cyclohexanone and 20 ml of solvent distilled off under vacuum. To this was added 4.54 g. aluminum isopropoxide and the reaction mixture refluxed overnight for 15 hours. The mixture was cooled, diluted with ethyl acetate, washed with sodium potassium tartarate, brine, and the organic layer was concentrated under vacuum and the residue steam distilled. The residue was extracted with ethyl acetate, washed with brine, dried and purified by column chromatography on silica gel, eluting with 5% EtOAc/hexane to yield the title compound.

Step 6: Synthesis of 7β-methyl-androst-5-en-3-one-17β-ol, t-butyldimethylsilyl ether.

To a solution of 370 mg of the product of the previous synthesis, in 5.5 ml ammonia, 1 ml THF, 1 ml. toluene, was added 50 mg. of metallic lithium in small pieces. After stirring the blue solution for 2 hours, a solution of 1,2-dibromethane in 2 ml THF was added. After stirring the solution at −78° C. for 10 minutes, 250 mg of ammonium chloride was added and the mixture stirred for 10 minutes. The excess ammonia was removed by evaporation under a nitrogen steam. The reaction mixture was diluted with brine, extracted with ethyl acetate. The organic layer was washed with brine, dried and concentrated to yield crude material which was used as such in the next synthesis.

Step 7: Synthesis of 7β-methyl-androst-4-en-3-on-17β-ol, t-butyldimethylsilyl ether To a solution of the product of the previous synthesis, being 432 mg in 4 ml THF was added 150 microliters DBU (1,8-diaza-bicyclo[5.4,0] undec-7-ene under nitrogen with stirring. The mixture was refluxed for 1.5 hours, then cooled, diluted with NH$_4$Cl solution. The solvent THF was removed under vacuum and the residue extracted with ethyl acetate. The organic layer was washed with brine, dried and concentrated under reduced pressure to yield crude material. The titled product was purified by chromatography on silica gel using 10% EtOAc/hexane as eluant.

Step 8: Synthesis of 17β-(t-butyldimethylsilyloxy)-7β-methyl-5-oxo-A-nor-3,5-secoandrostan-3-oic acid.

To a solution of 884 mg of the product of the previous synthesis in 15 ml. t-butyl alcohol at 80° C. was added 248 mg sodium carbonate in 1.5 ml water followed by a dropwise addition over 15–20 minutes of a mixture of 2.273 g sodium periodate with 16.8 mg potassium permanganate in 8 ml. water. The reaction mixture was heated at 80° C. for 2 hours, cooled, filtered, the residue washed with water, and then the extract L- concentrated under vaccum. The extract was acidified with aqueous HCl extracted with ethyl acetate and the organic layer washed with aqueous NaHSO$_3$, brine, dried and concentrated to yield crude 9. The proton NMR confirmed the assigned structure.

Step. 9: Synthesis of 4,7β-dimethyl-4-aza-androst-5-en-3-one-17β-ol, t-butyldimethylsilyl ether To a solution of the product of the previous synthesis, 840 mg in 5 ml ethylene glycol, was added 1.5 g sodium acetate and 737 mg. methylamine hydrochloride. After stirring the reaction mixture 4 hours at 180° C., the mixture was cooled, diluted with water, extracted with ethyl acetate, dried and concentrated to afford crude title compound. Proton NMR confirmed the assigned structure.

Step 10: Synthesis of 4,7β-dimethyl-4-aza-androst-5-en-3-one-17β-ol.

To a solution of 700 mg of the product of the previous example, in 20 ml of acetonitrile at 0° C., was added 500 microliters. aqueous HF. After stirring the reaction mixture for one hour, the HF was neutralized with aqueous sodium carbonate, diluted with water, acetonitrile removed under vacuum, and the residue extracted with ethyl acetate. The organic layer was dried, concentrated to give crude title compound which was further purified by preparative chromatography on silica gel using 3:1 chloroform/acetone.

Step 11: Synthesis of 4,7β-dimethyl-4-aza-androstan-3-one-17β-ol.

To a solution of the product of the previous synthesis, being 350 mg in 10 ml acetic acid was added 100 mg platinum dioxide and the resulting mixture was evacuated and flushed with hydrogen. The reaction was shaken overnight at room temperature under 40 Psig hydrogen pressure. The solution was filtered concentrated. The residue was worked up with ethyl acetate, the organic layer was then concentrated under vacuum, diluted with ethyl acetate, washed with aqueous NaHCO$_3$, brine, dried, concentrated to yield the title compound. Mass Spec: 320 (M+1).

Step 12: Synthesis of 4-aza-4,7β-dimethyl-5α-androstan-3, 17-dione

The product of the previous synthesis, 1.013 g (3.176 mmol) was placed with 6 ml methylene chloride into a dry flask. Powdered molecular 4Å sieves, 1.6 g, and 0.558 g (4.76 mmol) of N-methylmorpholine-N-oxide (NMO) and then tetrapropylammonium perruthanate (TPAP), 55 mg (0.159 mmol) were added. The reaction was stirred for 2 hours, diluted with 150 ml ethyl acetate and filtered. The tiltrate was evaporated to dryness to yield crude product which was recrystallized from EtOAc to yield pure product, mp 135°–138° C.

Elemental Analysis Calc'd for C$_{20}$H$_{31}$NO$_2$, mw=317.48, Calc'd: C, 75.67; H, 9.84; N, 4.41, Found: C, 75.16; H, 10.22; N, 4.13 Mass Spec. 318 (M+1).

While the invention has been described and illustrated with reference to certain particular embodiments thereof, those skilled in the art will appreciate that various changes, modifications and substitutions can be made therein without departing from the spirit and scope of the invention. For example, effective dosages other than the particular dosages as set forth herein above may be applicable as a consequence of variations in the responsiveness of the mammal being treated for any of the indications for the compounds of the invention indicated above. Likewise, the specific pharmacological responses observed may vary according to and depending upon the particular active compound selected or whether there are present pharmaceutical carriers, as well as the type of formulation and mode of administration employed, and such expected variations or differences in the results are contemplated in accordance with the objects and practices of the present invention. It is intended, therefore, that the invention be defined by the scope of the claims which follow and that such claims be interpreted as broadly as is reasonable.

What is claimed is:

1. A method of treating a condition selected from apocrine gland sweating, hyperhidrosis, and hydradenitis suppurativa comprising administering to a person in need of such treatment a therapeutically effective amount of a 5α-reductase inhibitor.

2. The method of claim 1 wherein the inhibitor is a 5α-reductase type 2 inhibitor.

3. The method of claim 2 further comprising the administration of a 5α-reductase type 1 inhibitor.

4. The method of claim 3 wherein the 5α-reductase 2 inhibitor is finasteride and the 5α-reductase type 1 inhibitor is selected from 3-oxo-4-aza-4,7β-dimethyl-16β-(phenoxy)-5α-androstane, and 3-oxo-4-aza-4,7β-dimethyl-16β-(4-chlorophenoxy)-5 α-androstane.

5. The method of claim 1 wherein the inhibitor is a 5α-reductase type 1 inhibitor.

6. The method of claim 5 wherein the inhibitor is selected from 3-oxo-4-aza-4,7β-dimethyl-16β-(phenoxy)-5α-androstane, and 3-oxo-4-aza-4,7β-dimethyl-16β-(4-chlorophenoxy)-5α-androstane.

7. The method of claim 1 wherein the inhibitor is a dual 5α-reductase type 1 and type 2 inhibitor.

8. The method of claim 1 wherein the condition is apocrine gland sweating, and further comprising administration of a therapeutically effective amount of aluminum hydroxide.

9. The method of claim 1 wherein the condition is hyperhidrosis, and further comprising administration of a therapeutically effective amount of aluminum hydroxide.

10. The method of claim 1 wherein the condition is hydradenitis suppurativa, and further comprising administration of a therapeutically effective amount of isotretinoin.

11. The method of claim 1 wherein the 5α-reductase inhibitor is administered orally.

12. The method of claim 1 wherein the 5α-reductase inhibitor is administered topically.

13. A pharmaceutical composition comprising
   (a) a pharmaceutically acceptable carrier,
   (b) a therapeutically effective amount of a 5α-reductase inhibitor, and
   (c) a therapeutically effective amount of a compound selected from an antiperspirant, isotretinoin, and combinations thereof.

14. A composition of claim 13 wherein the antiperspirant is an aluminum salt.

15. A composition of claim 14 wherein the aluminum salt is aluminum hydroxide.

16. A pharmaceutical composition comprising
   (a) a pharmaceutically acceptable carrier,
   (b) a therapeutically effective amount of a 5α-reductase type 1 inhibitor, and a 5α-reductase type 2 inhibitor, and
   (c) a therapeutically effective amount of a compound selected from an antiperspirant, isotretinoin, and combinations thereof.

* * * * *